United States Patent [19]
Scherz et al.

[11] Patent Number: 5,684,002
[45] Date of Patent: Nov. 4, 1997

[54] DIHYDORBENZOFURAN AND RELATED COMPOUNDS USEFUL AS ANTI-INFLAMMATORY AGENTS

[75] Inventors: Michael Wiard Scherz; John Michael Janusz, both of West Chester, Ohio

[73] Assignee: The Procter & Gamble Company, Cincinnati, Ohio

[21] Appl. No.: 486,876

[22] Filed: Jun. 7, 1995

Related U.S. Application Data

[63] Continuation-in-part of Ser. No. 301,456, Sep. 7, 1994, abandoned.

[51] Int. Cl.$^6$ .................. A61K 31/34; C07D 307/79
[52] U.S. Cl. .................. 514/228.2; 514/233.5; 514/320; 514/462; 514/469; 544/153; 544/376; 544/62; 546/196; 546/316; 548/200; 548/525; 549/345; 549/462; 549/57
[58] Field of Search .................. 549/345, 462, 549/57; 514/462, 469

[56] References Cited

U.S. PATENT DOCUMENTS

| 4,130,666 | 12/1978 | Moore | 424/331 |
| 4,670,457 | 6/1987 | Doria et al. | 514/470 |
| 4,708,966 | 11/1987 | Loomans et al. | 514/689 |
| 4,849,428 | 7/1989 | Dobson et al. | 549/307 |

FOREIGN PATENT DOCUMENTS

| 848 496 | 5/1977 | Belgium . | |
| A 0 059 884 | 9/1982 | European Pat. Off. | C07D 307/79 |
| A 0 132 130 | 1/1985 | European Pat. Off. | C07C 307/79 |
| A 0 234 872 | 9/1987 | European Pat. Off. | C07D 307/79 |
| 0 321 432 | 6/1989 | European Pat. Off. | C07C 45/46 |
| A 0 322 004 | 6/1989 | European Pat. Off. | C07D 307/79 |
| A 0 652 214 | 5/1995 | European Pat. Off. | C07D 307/91 |
| 52-3052 | 1/1977 | Japan | A61K 31/33 |
| 53-5178 | 1/1978 | Japan | A61K 31/49 |
| 53-82788 | 7/1978 | Japan | A61K 31/49 |
| 1246 272 | 10/1989 | Japan | A61K 31/34 |
| 1 304 108 | 1/1973 | United Kingdom | C07D 5/42 |
| 1 565 080 | 4/1980 | United Kingdom | A61K 31/13 |
| 2 169 893 | 12/1984 | United Kingdom | C07D 307/78 |

OTHER PUBLICATIONS

Chakrabarti, J.K., R.J. Eggleton, P.T. Gallagher, J. Harvey, T.A. Hicks, E.A. Kitchen and C. W. Smith, "5–Acyl–3–substituted–benzofuran–2(3H)–ones as Potential Antiinflammatory Agents", *J. Med. Chem.*, vol. 30 (1987), pp. 1663–1668.

Hammond, M.L., I.E. Kopka, R.A. Zambias, C.G. Caldwell, J. Boger, F. Baker, T. Bach, S. Luell and D.E. MacIntyre, "2,3–Dihydro–5–benzofuranols as Antioxidant–based Inhibitors of Leukotriene Biosynthesis", *J. Med. Chem.*, vol. 32 (1989), pp. 1006–1020.

Ortiz de Montellano, P.R. and M.A. Correia, "Suicidal Destruction of Cytochrome P–450 During Oxidative Drug Metabolism", *Ann. Rev. Pharmacol. Toxicol.*, vol. 23 (1983), pp. 481–503.

U.S. application No. 08/280,892, M. W. Scherz, filed Jul. 27, 1994.

*Primary Examiner*—Bernard Dentz
*Attorney, Agent, or Firm*—Mary Pat McMahon; Karen F. Clark; Milton B. Graff, IV

[57] ABSTRACT

A compound having the structure:

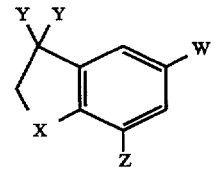

wherein
(a) W is —C(X')—NRR' or —NR—C(X')R';
(b) X and X' are independently O or S;
(c) each Y is independently hydrogen or straight, branched or cyclic alkanyl having from 1 to about 3 carbon atoms, or the two Y's are bonded to form an alkanyl ring having from 3 to about 7 carbon atoms;
(d) Z is unsubstituted branched or cyclic alkyl, or unsubstituted or alkanyl-substituted phenyl or benzyl, Z having from 3 to about 10 atoms other than hydrogen;
(e) R and R' are each independently selected from hydrogen, hydroxy straight, branched or substituted alkyl having from 1 to about 6 carbon atoms, and cyclic alkyl having from 3 to about 7 carbon atoms; unsubstituted or substituted aryl, heteroaryl or heterocyclic groups; or R and R' are bonded together to form a ring having from from 3 to about 8 atoms wherein about 1 to about 4 atoms may be heteroatoms;

pharmaceutical compositions comprising such compounds, and methods of treating inflammation or pain using such compounds.

17 Claims, No Drawings

DIHYDORBENZOFURAN AND RELATED COMPOUNDS USEFUL AS ANTI-INFLAMMATORY AGENTS

This application is a continuation-in-part of U.S. Ser. No. 08/301,456, filed Sep. 7, 1994 now abandoned.

TECHNICAL FIELD

The subject invention relates to nonsteroidal anti-inflammatory drugs, particularly to substituted dihydrobenzofuran and related compounds.

BACKGROUND OF THE INVENTION

Certain dihydrobenzofuran compounds and other compounds structurally related thereto have been found to have significant disease altering activities. Such compounds, processes for making them, and uses for them are disclosed in the following references: U.S. Pat. No. 4,670,457 issued to Doria, Romeo & Corno on Jun. 2, 1987; U.S. Pat. No. 4,849,428 issued to Dobson, Loomans, Mathews & Miller on Jul. 18, 1989; Japanese Patent Publication No. 53-005178 of Yoshitomi Pharm. Ind. KK published Jan. 1, 1978; Hammond, M. L., I. E. Kopka, R. A. Zambias, C. G. Caldwell, J. Boger, F. Baker, T. Bach, S. Luell & D. E. MacIntyre, "2,3-Dihydro-5-benzofuranols as Antioxidant-Based Inhibitors of Leukotriene Biosynthesis", *J. Med. Chem.*, Vol. 32 (1989), pp. 1006–1020; Ortiz de Montellano, P. R & M. A. Correia, "Suicidal Destruction of Cytochrome P-450 during Oxidative Drug Metabolism", *Ann. Rev. Pharmacol. Toxicol.*, Vol. 23 (1983), pp. 481–503; Chakrabarti, J. K., R. J. Eggleton, P. T. Gallagher, J. Harvey, T. A. Hicks, E. A. Kitchen, and C. W. Smith, "5-Acyl-3-substituted-benzofuran-2(3H)-ones as Potential Anti-inflammatory Agents", *J. Med. Chem.*, Vol. 30 (1987), pp. 1663–1668.

It is an object of the subject invention to provide compounds which have effective anti-inflammatory, analgesic and/or anti-oxidant activity.

It is a further object of the subject invention to provide such compounds which cause few adverse side effects.

It is also an object of the subject invention to provide methods for treating inflammation and/or pain using the subject compounds.

SUMMARY OF THE INVENTION

The subject invention compounds having the structure:

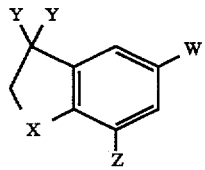

wherein
(a) W is —C(X')—NRR' or —NR—C(X')R';
(b) X and X' are independently O or S;
(c) each Y is independently hydrogen or unsubstituted straight, branched or cyclic alkanyl having from 1 to about 3 carbon atoms, or the two Y's are bonded to form an unsubstituted alkanyl ring having from 3 to about 7 carbon atoms;
(d) Z is unsubstituted branched or cyclic alkyl, or unsubstituted or alkanyl-substituted phenyl or benzyl, Z having from 3 to about 10 atoms other than hydrogen; and
(e) R and R' are each independently selected from hydrogen, hydroxy straight, branched or substituted alkyl having from 1 to about 6 carbon atoms, and cyclic alkyl having from about 3 to about 7 carbon atoms; unsubstituted or substituted aryl, heteroaryl or heterocyclic groups; or R and R' are bonded together to form a ring having from from 3 to about 8 atoms wherein from about 1 to about 4 atoms may be heteroatoms.

DETAILED DESCRIPTION OF THE INVENTION

As used herein, unless otherwise indicated, "alkyl" means a straight, branched or cyclic hydrocarbon chain, saturated or unsaturated, unsubstituted or substituted and may contain heteroatoms such as oxygen, sulfur or nitrogen within the alkyl chain. Preferred alkyl are $C_1$–$C_{12}$; more preferred are $C_1$–$C_6$; more preferred still are $C_1$–$C_3$. Preferred alkyl are straight chain. Preferred branched alkyl have one or two branches, preferably one branch. Preferred cyclic alkyl are monocyclic or are a straight chain with a monocyclic terminus. Preferred alkyl are saturated. Unsaturated alkyl have one or more double bonds or/and one or more triple bonds. Preferred unsaturated alkyl have one or two double bonds or one triple bond, more preferably one double bond. Preferred alkyl are unsubstituted. Preferred substituted alkyl are mono-, di-, or trisubstituted. Preferred alkyl substituents include halo, hydroxy, alkoxy (e.g., methoxy, ethoxy, propoxy, butoxy, pentoxy), aryloxy (e.g., phenoxy, chlorophenoxy, tolyloxy, methoxyphenoxy, benzyloxy, alkyloxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkyloxycarbonylphenylthio), aryl (e.g., phenyl, tolyl, alkyloxphenyl, alkyloxycarbonylphenyl, halophenyl), heterocyclyl, heteroaryl, amino (e.g., amino, mono- and di- $C_1$–$C_3$ alkanylamino, methylphenylamino, methylbenzylamino, $C_1$–$C_3$ alkanylamido, carbamamido, ureido, guanidino).

As used herein, "alkanyl" means a saturated alkyl.

As used herein, "alkoxy" means —O—alkyl.

As used herein, "aryl" means a moiety having an unsubstituted or substituted aromatic ring having 6 to about 10 carbon atoms. Preferred aryl are phenyl and naphthyl; most preferred aryl is phenyl. Preferred aryl are unsubstituted. Preferred substituted aryl are mono-, di-, or trisubstituted, more preferably monosubstituted. Preferred aryl substituents include hydroxy, mercapto, halo, methyl, ethyl and propyl.

As used herein, "heterocyclyl" means a moiety having a saturated or unsaturated non-aromatic ring having from 3 to about 8 ring atoms, including from 2 to about 6 carbon atoms and from 1 to about 4 heteroatoms selected from O, S, and N. Preferred heterocycles are saturated. Preferred heterocycles have 5 or 6 atoms in the ring including 1 or 2 heteroatoms in the ring, also preferably 1 heteroatom in the ring. Specific preferred heterocycles include piperidinyl, tetrahydrothienyl, pyrrolidinyl, piperazinyl, morpholinyl, tetrahydropyranyl, tetrahydrofuranyl, imidazolidinyl, pyrazolidinyl, oxazolidinyl, isoxazolidinyl, oxathiazolidinyl, isothiazolidinyl, azepinyl, oxepinyl, triazolidinyl. Heterocycles are unsubstituted or substituted, preferably unsubstituted. Preferred substituted heterocycles are mono-, di-, or trisubstitued, more preferably monosubstituted. Preferred heterocycle substitutents include alkyl, halo, hydroxy, alkoxy, thio, amino, amido, ureido, guanidino, thiocarbamamido, thioureido.

As used herein, "heteroaryl" means a moiety having an aromatic ring having 5 or 6 ring atoms including from 2 to 5 carbon atoms and from 1 to 3 heteroatoms selected from O, S and N. Preferred heteroaryls have 1 or 2 heteroatoms in the ring, also preferably 1 heteroatom in the ring. Specific preferred heteroaryls include pyrrolyl, imidazolyl, pyridyl, pyrimidinyl, pyrazinyl, oxazolyl, isoxazolyl, pyranyl, thienyl, tetrazolyl, thiazolyl, isothiazolyl, furyl, oxathiazolyl. Heteroaryls are unsubstituted or substituted, preferably unsubstituted. Preferred substituted heterocycles are mono-, di-, or trisubstituted, more preferably monosubstituted. Preferred heteroaryl substituents include alkyl, halo, hydroxy, alkoxy, thio, amino, amido, ureido, guanidino, thiocarbamamido, thiouredio.

As used herein, "halo" means fluoro, chloro, bromo or iodo. Preferred halo are fluoro, chloro and bromo; more preferred are chloro and bromo, especially chloro.

Compounds

The subject invention involves compounds having the following structure:

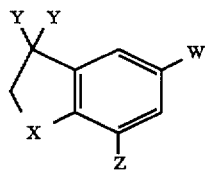

In the above structure, W is:

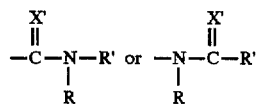

In the above structure, X and X' are independently O or S. Preferred X is O. Preferred X' is O.

In the above structure, each Y is independently selected from hydrogen, unsubstituted straight or branched alkanyl having from 1 to about 3 carbon atoms, and cyclic alkyl having about 3 carbon atoms, cyclopropyl, or the Y's are bonded together to form an unsubstituted cyclic alkanyl ring having from 3 to about 7 carbon atoms in the ring. Each Y is preferably hydrogen, methyl, ethyl or cyclopropyl; more preferably hydrogen or methyl; most preferably methyl. Preferably both Y's are the same. When the Y's are bonded together to form a cyclic ring, the ring is preferably cyclopropyl, cyclobutyl or cyclopentyl, more preferably cyclopropyl.

In the above structure, Z is selected from unsubstituted branched or cyclic alkyl, and unsubstituted or alkanyl-substituted phenyl, or benzyl, Z having from 3 to about 10 atoms other than hydrogen. Z is preferably saturated.

Z is preferably branched alkanyl having from about 3 to about 8 carbon atoms, more preferably from about 4 to about 6 carbon atoms. Z is preferably branched alkanyl having 2 or more branches, more preferably 2 branches. Preferred branched alkanyl Z include t-butyl, neopentyl, isopropyl; most preferred is t-butyl. Preferred cyclic alkanyl Z include cyclopropyl, cyclobutyl, cyclopentyl, cyclohexyl, cycloheptyl. Also preferred cyclic alkanyl Z include methyl or ethyl with a terminal cyclopropyl, cyclobutyl or cyclopentyl, especially cyclopropylmethyl or cyclopropylethyl. Also preferred Z is unsubstituted phenyl or benzyl.

R and R' are each independently selected from hydrogen, hydroxy straight, branched or substituted alkyl having from 1 to about 6 carbon atoms, and cyclic alkyl having from 3 to about 7 carbon atoms; unsubstituted or substituted aryl, heteroaryl or heterocyclic groups; or R and R' are bonded together to form a ring having from from 3 to about 7 atoms wherein one to three atoms may be heteroatoms Preferred R is selected from hydrogen, straight or branched alkyl having from 1 to about 6 carbon atoms, and cyclic alkyl having from 3 to about 6 carbon atoms. R preferably has from 0 to about 10, more preferably from 0 to about 6, atoms other than hydrogen. Preferably alkyl portions of R are saturated. More preferred R is hydrogen, methyl or ethyl.

Preferred R' is selected from hydrogen, hydroxy, straight or branched alkyl or alkoxy having from 1 to about 6 carbon atoms, and cyclic alkyl having from 3 to about 7 carbon atoms. R' preferably has from 0 to about 10, more preferably from 0 to about 6, atoms other than hydrogen. Preferably alkyl portions of R' are saturated. Preferred R' is $C_{1-C5}$ straight or branched alkanyl. Preferred R' is $C_1$–$C_5$ straight or branched alkanoxy. Preferred R' is $C_3$–$C_6$ cyclic alkanyl. Also preferred is straight chain alkanyl, preferably methyl or ethyl, with a terminal cyclopropyl, cyclobutyl or cyclopentyl; especially cyclopropylmethyl. More preferred R' is selected from methyl, ethyl, n-propyl, i-propyl, n-butyl, I-methylbutyl, ethoxy, benzyl, phenethyl, cyclopropyl, cyclohexyl, cyclopropylmethyl, 2-methoxyethyl, 2-thiazolyl, 2-thiazolinyl, and 3-pyridyl. Most preferred R' is selected from ethyl, i-propyl, n-propyl, cyclopropyl, 2-methoxyethyl, thiazolinyl and ethoxy.

R is preferably unsubstituted. R' is preferably unsubstituted. Preferred substituents for substituted alkyl R or R' include hydroxy, mercapto, halo, amino, alkoxy, alkylamino, dialkylamino, carboxy, carboxyalkyl, phenyl, halophenyl, alkylphenyl, alkoxyphenyl, carboxyphenyl, carboxyalkylphenyl, pyridyl, alkylpyridyl, halopyridyl, alkoxypyridyl, carboxypyridyl, and carboxyalkylpyridyl.

R and R' can be joined in a ring having from about 3 to about 8 atoms, where one to four of these atoms may be heteroatoms. Preferrred are pyrrolidinyl, piperidinyl, thiomorpholinyl, piperizinyl and morpholinyl.

Preferred compounds of the subject invention include those having the above structure with W, X, X', R, R', the two Y's, and Z as indicated in the following table:

| Compound No. | W | X | X' | R | R' | Y | Z |
|---|---|---|---|---|---|---|---|
| 1 | C(X')NRR' | O | O | H | Me | Me, | Me t-Bu |
| 2 | C(X')NRR' | O | O | H | Et | Me, | Me t-Bu |
| 3 | C(X')NRR' | O | O | H | n-Pr | Me, | Me t-Bu |
| 4 | C(X')NRR' | O | O | H | n-Bu | Me, | Me t-Bu |
| 5 | C(X')NRR' | O | O | H | 2-Pe | Me, | Me t-Bu |
| 6 | C(X')NRR' | O | O | H | OEt | Me, | Me t-Bu |

-continued

| Compound No. | W | X | X' | R | R' | Y | Z |
|---|---|---|---|---|---|---|---|
| 7 | C(X')NRR' | O | O | H | c-Pr | Me, | Me t-Bu |
| 8 | C(X')NRR' | O | O | H | $CH_2$-c-Pr | Me, | Me t-Bu |
| 9 | C(X')NRR' | O | O | Me | Et | Me, | Me t-Bu |
| 10 | C(X')NRR' | O | S | H | n-Pr | Me, | Me t-Bu |
| 11 | NRC(X')R' | O | O | H | Me | Me, | Me t-Bu |
| 12 | NRC(X')R' | O | O | H | Et | Me, | Me t-Bu |
| 13 | C(X')NRR' | O | O | H | $CH_2CH_2OMe$ | Me, | Me t-Bu |
| 14 | C(X')NRR' | O | O | H | $CH_2CH(OH)CH_2OH$ | Me, | Me t-Bu |
| 15 | C(X')NRR' | O | O | H | 2-thiazolyl | Me, | Me t-Bu |
| 16 | C(X')NRR' | O | O | H | 2-thiazolinyl | Me, | Me t-Bu |
| 17 | C(X')NRR' | O | O | H | 3-pyridyl | Me, | Me t-Bu |
| 18 | C(X')NRR' | O | O | Me | c-Pr | Me, | Me t-Bu |
| 19 | C(X')NRR' | O | O | R/R' = pyrrolidinyl | | Me, | Me t-Bu |
| 20 | C(X')NRR' | O | O | R/R' = piperidinyl | | Me, | Me t-Bu |
| 21 | C(X')NRR' | O | O | R/R' = thiomorpholinyl | | Me, | Me t-Bu |
| 22 | C(X')NRR' | O | O | R/R' = piperizinyl | | Me, | Me t-Bu |

In order to determine and assess pharmacological activity, testing of the subject compounds in animals is carried out using various assays known to those skilled in the art. The anti-inflammatory activity of the subject compounds can be conveniently demonstrated using an assay designed to test the ability of the subject compounds to antagonize the local edema which is characteristic of the inflammatory response. Examples of such known tests include the rat carrageenan edema test, the oxazolone-induced inflamed mouse ear test, and the mouse arachadonic acid-induced inflamed ear test. Analgesic activity may be tested in art-known models such as the phenylbenzoquinone-induced writhing test in mice, and the Randall & Selitto test in rats. Another useful art-known test is the rat adjuvant arthritis test which is a useful model for assessing anti-inflammatory activity, anti-arthritic and anti-resorptive activity in a chronic, rather than an acute, model.

These and other appropriate tests for pharmacological activity are disclosed and/or referred to in U.S. Pat. No. 4,130,666 issued to Moore on Dec. 19, 1978; U.S. Pat. No. 4,431,656 issued Feb. 14, 1984 to Katsumi, et al.; U.S. Pat. No. 4,440,784 issued to Katsumi, et al. on Apr. 3, 1984; Japanese Patent Application 85/54315 of Katsumi, et al., published Mar. 28, 1985; European Patent Application No. 0,059,090 of Yamanuchi Pharmaceutical Company Ltd., published Sep. 1, 1982; Opas, E. V., R. J. Bonney & J. L. Humes, "Prostaglandin and Leukotriene Synthesis in Mouse Ears Inflamed by Arachadonic Acid", *The Journal of Investigative Dermatology*, Vol. 84, No. 4 (1985), pp. 253–256; Swingle, K. F., R. L. Bell & G. G. I. Moore, "Anti-inflammatory Activity of Antioxidants", *Anti-inflammatory and Antirheumatic Drugs*, Vol. III, Chapter 4, K. D. Rainsford, ed., CRC Press, Inc., (1985), pp. 105–126; Adamkiewicz, V. W., W. B. Rice & J. D. McColl, "Antiphlogistic Effect of Trypsin in Normal and in Adrenalectomized Rats", *Canadian Journal of Biochemistry & Physiology*, Vol. 33 (1955), pp. 332–339; Sellye, H., "Further Studies Concerning the Participation of the Adrenal Cortex in the Pathogenesis of Arthritis", *British Medical Journal*, Vol. 2 (1949), pp. 1129–1135; and Winter, C. A., E. A. Risley & G. W. Nuss, "Carrageenan-Induced Edema in Hind Paw of the Rats as an Assay for Antiinflammatory Drugs" *Proceedings of Society of Experimental Biology and Medicine*, Vol. 111 (1962), pp. 544–547; Otterness, I., & M. L. Bliven, "Laboratory Methods for Testing Nonsteroidal Antiinflammatory Drugs", *Nonsteroidal Antiinflammatory Drugs*, Chapter 3, J. G. Lombardino, ed., John Wiley & Sons, Inc. (1985), pp. 111–252. Hitchens, J. T., S. Goldstein, L. Shemano & J. M. Beiler, "Analgesic Effects of Irritants in Three Models of Experimentally-Induced Pain", *Arch. Int. Pharmacodyn*, Vol. 169, No. 2 (1967) pp. 384–393; Milne, G. M. & T. M. Twomey, "The Analgetic Properties of Piroxicam in Animals and Correlation with Experimentally Determined Plasma Levels", *Agents and Actions*, Vol. 10, No. ½ (1980), pp. 31–37; Randall, L. O. & J. J. Selitto, "A Method for Measurement of Analgesic Activity on Inflamed Tissue", *Arch. Int. Pharmacodyn.*, Vol. 111, No. 4 (1957), pp. 409–419; Winter, C. A. & L. Faltaker, "Nociceptive Thresholds as Affected by Parenteral Administration of Irritants and of Various Antinociceptive Drugs", *J. Pharmacol. Exp. Ther.*, Vol. 148, No. 3 (1965), pp. 373–379; the disclosure of all these references are incorporated herein by reference.

Many anti-inflammatory drugs, particularly non-steroidal anti-inflammatory drugs (NSAIDs) cause undesirable gastrointestinal side effects, especially when dosed perorally; such side effects may include ulcers and erosions. These side effects, which are often asymptomatic, can become serious enough to require hospitalization and can even be lethal. Compounds of the subject invention generally cause fewer such gastrointestinal side effects compared to other NSAIDs. Some compounds of the subject invention are even gastroprotective, protecting the stomach and intestines from ulcers and erosions, particularly those caused by ethanol or other NSAIDs.

Certain NSAIDs, when dosed systematically, cause an undesirable increase in systemic levels of certain liver enzymes. Compounds of the subject invention generally cause little or no liver enzyme side effects.

Compounds useful in the subject invention can be made using the following general reaction scheme:

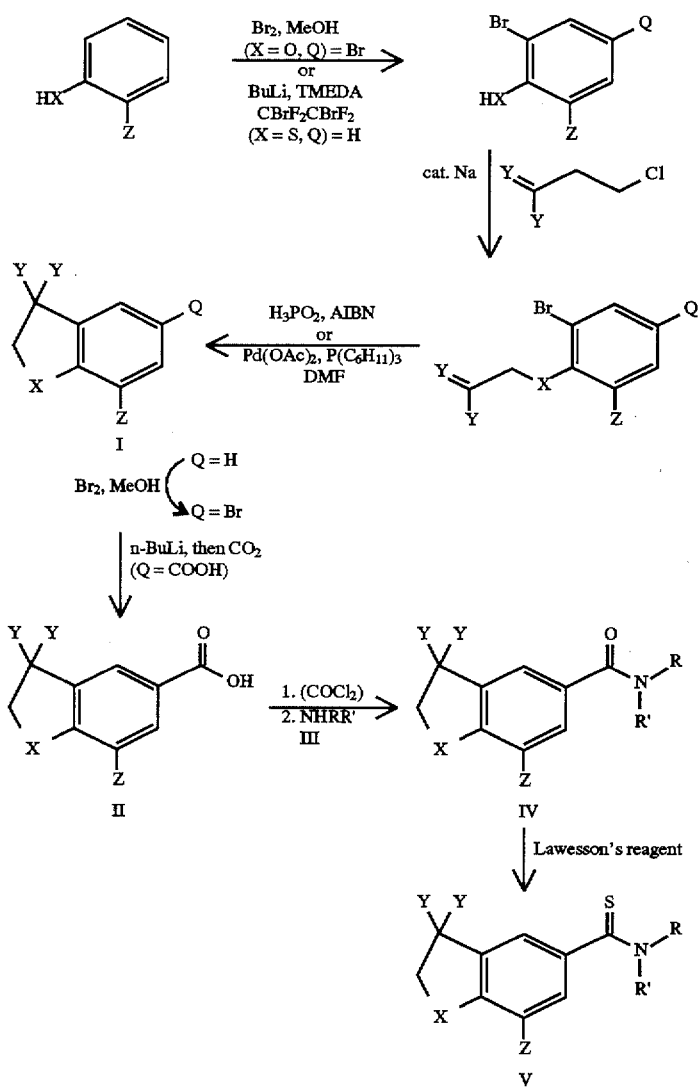

Scheme 1

A general method for the preparation of compounds of structure IV in Scheme 1 is the condensation of an appropriate heterocyclic carboxylic acid of structure II with an appropriate amine of structure III under known reaction conditions. For example, this reaction can be performed by activation of the carboxylic acid in an inert halogenated solvent, such as $CH_2Cl_2$, using an agent such as oxayl chloride at the appropriate temperature, followed by evaporation of the volatiles, and reaction with the appropriate amine. In general the organic amines useful for this reaction are known, commercially available, or readily prepared. Alternatively, the compounds of structure IV in Scheme I can be prepared by carboamidation of the appropriate heterocyclic bromide of structure I using a catalytic amount of a palladium complex such as bis(triphenylphosphine) palladium dichloride in the presence of carbon monoxide gas and excess of the appropriate amine (structure III) at elevated temperature and pressure. Acids of general structure II may be prepared by a substantially similar method, in which the carbonylation is performed in the presence of a palladium complex, a non-volatile tertiary amine such as tri-n-butylamine and excess alcohol such as ethanol, followed by alkaline hydrolysis and acidification.

Compounds of structure I are made by a series of reactions culminating in a cyclization reaction illustrated in Scheme 1. Reaction conditions useful for achieving this cyclization are known, and involve either the intermediacy of, for example, free radical species, or Pd or Ni coordination complexes. Thus, appropriate reaction conditions for achieving this transformation, are for example, treatment with a reductant such as tri-n-butyltinhydride, tris-trimethylsilylsilane, or hypophosphorus acid in hot dioxane, in the presence of a radical chain initiator such as azo-bis-isobutyrylnitrile. Alternatively, the ring closure can be achieved in hot dimethylformamide solvent with $Pd^{2+}$ or $Ni^{2+}$ salts in the presence of trivalent alkyl or aryl phosphorous compounds such as tricyclohexylphosphine, triphenylphosphine or trimethylphosphine.

The substrates for the cyclization reaction are obtained by allylation of an appropriately substituted phenol or thiophenol with an allylic halide such as 3-chloro-2-methylpropene, 1-chloro-2-methyl-2-butene, 1-chloromethylcyclopen-tene, or 1-chloromethylcyclobutene using known reaction conditions. For example 3-chloro-2-methylpropene in the presence of catalytic sodium iodide in refluxing acetone reacts with substituted phenols or thiophenols to provide the allylated materials.

The substituted phenols or thiophenols are either known, commercially available, or readily prepared by known methods. For example, 2,4-dibromo-6-t-butylphenol is obtained by reaction of 2-t-butylphenol with bromine in MeOH, and 2-bromo-6-t-butylthiophenol is obtained by treatment of 2-t-butylthiophenol with excess alkyl lithium reagent in a strongly coordinating solvent such as tetramethylethylenediamine or hexamethylphosporamide followed by reaction with 1,2-dibromo-tetrafluoroethane in an ethereal solvent at low temperature.

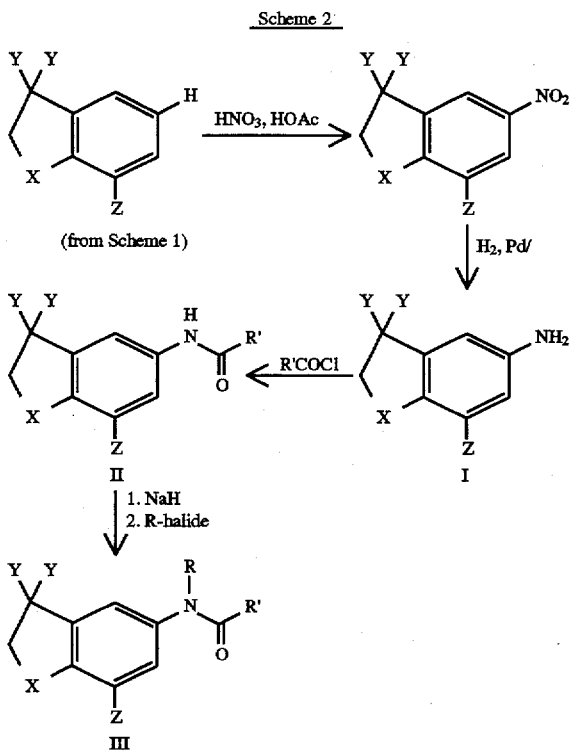

Scheme 2

A general method for the preparation of compounds of structure III in Scheme 2 is the acylation of structure I in Scheme 2 with an appropriate acid chloride under reaction conditions which are known. For example, this reaction can be performed in $CH_2Cl_2$ in the presence of a catalytic amount of N,N-dimethyl-4-aminopyridine. Amides of structure II or III may be converted to the corresponding thioamides using Lawesson's reagent. Amides of structure II in Scheme 2 or the corresponding thioamides may be converted to compounds of structure III by a known sequence of deprotonation/alkylation, employing the desired alkyl halide, for instance, as the alkylating reagent. It is known that in certain circumstances it is necessary to protect either the N, S, or O of intermediates during the preparation of compounds which are the subject of this invention. Introduction and removal of suitable N, S, or O protecting groups are known: see, for example, "Protective Groups in Organic Chemistry," J. F. W. McOmie, Advances in Organic Chemistry 3:159-190 (1963), and T. W. Greene, P. G. M. Wuts "Protecting Groups in Organic Synthesis," Wiley (New York), 1991. The use of appropriate protecting groups is implied by the processes depicted herein, when not expressly illustrated.

SYNTHESIS EXAMPLES

The following non-limiting examples provide further information regarding synthesis of the subject compounds.

Example 1

Synthesis of N-propyl (7-tert-butyl-3,3-dimethyl-2,3-dihydrobenzo[b]furan-5-yl)carboxamide

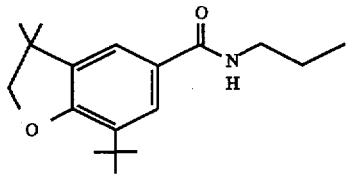

2,4-dibromo-6-tert-butylphenol

In a 2 L 3-neck flask, equipped with Ar inlet, reflux condenser, addition funnel, and efficient magnetic stir bar, is placed 2-tert-butylphenol (150.2 g, 1.00 mol) and MeOH (300 mL). The stirred solution is cooled in an ice bath as neat $Br_2$ (321.6 g, 2.01 mol, 2.01 eq) is added dropwise over 0.5 h (Caution: this reaction is exothermic. Control with rate of addition.) The reaction is monitored by TLC (2% EtOAc/hexane), and is complete after 2 hrs. The reaction mixture is transferred to a 1 L beaker, along with a 20-mL rinse of the reaction flask. The red solution solidifies rapidly to a bright orange crystalline mass. The crystalline mass is redissolved by heating over a steam bath, and then a solution of $Na_2S_2O_5$ (1.45 g, 5.4 mmol) in 40 mL $H_2O$ is added, followed immediately by fresh MeOH (60 mL). The resulting suspension is reheated on the steam bath for 10 min (the mixture does not redissolve), and then is vigorously stirred while allowing to cool to room temperature. After 0.5 h, practically all yellow color has vanished, and faint orange white crystals are deposited. These are filtered and air dried to yield 2,4-dibromo-6-tert-butylphenol as faint orange-white platelets.

2,4-dibromo-6-tert-butylphenyl isobutenyl ether

In a 3000 mL 3-neck flask, equipped with Ar inlet and magnetic stirrer, is placed 2,4-dibromo-6-tert-butylphenol (70.0 g, 226 mmol), $K_2CO_3$ (37.6 g, 276 mmol, 1.2 eq), NaI (3.38 g, 22.6 mmol, 0.1 eq), p-methallyl chloride (33.9 mL, 339 mmol, 1.5 eq), and acetone (1500 mL). The reaction mixture is vigorously stirred at 23° C. for 56 hrs, and monitored by TLC analysis (pet. ether). The solids are removed by filtration, washed with acetone, and the filtrates rotoevaporated (bath temperature kept below 35° C.) to give an oil. The oil is dissolved in hexane (100 mL), and stirred with silica gel (80 g). The slurry is filtered through a pad of Celite, and eluted with additional hexane (6×100 mL). The filtrate is evaporated to give 2,4-dibromo-6-tert-butylphenyl isobutenyl ether as a yellow oil. The material is stored in the freezer and is used as soon as possible.

5-bromo-7-tert-butyl-3,3-dimethyl-2,3-dihydrobenzo[b]furan

Anhydrous hypophosphorus acid (275 g, 4.16 mol) is prepared by azeotropically removing water from commercial 50% aqueous solution (550 g) using toluene (5×500 mL). In a 5000 mL 3-neck flask, equipped with Ar bubbler and submersed Ar inlet, reflux condenser, addition funnel, and magnetic stirrer is placed dioxane (3000 mL), 2,4- dibromo-6-tert-butylphenyl isobutenyl ether (50.3 g, 0.14 mol), the anhydrous hypophosphorus acid (275 g, 4.16 mol) prepared above, and triethylamine (585 mL, 4.16 mol). An exotherm to 50° C. is apparent. The mixture is degassed by bubbling with Ar for 30 min, and then is maintained under an atmosphere of Ar. A solution of azo-bis-isobutyrylnitrile (AIBN) (20 mL of a 0.7M solution in de-gassed dioxane) is added via the addition funnel. The stirred solution is brought to reflux. Every 0.5 h, an additional 20 mL of the AIBN solution is added. The reaction is monitored by TLC for disappearance of starting material. After 3 h, further addition of AIBN is discontinued, the reaction is allowed to reflux an additional 14 h, and then is allowed to cool to 24° C. The reaction is twice extracted with a mixture of brine (250 mL) and 1N HCl (100 mL). The organic layer is dried over MgSO₄, filtered, and evaporated to give a yellow oil admixed with a white solid. This is triturated with hexane (300 mL), and the insolubles are filtered off, rinsed with fresh hexane (50 mL), and discarded. The hexanes are evaporated to give a 8:1 mixture of 5-bromo-7-tert-butyl-3, 3-dimethyl-2,3-dihydrobenzo[b]furan and its debromonated analog as colorless oil.

7-tert-butyl-3,3-dimethyl-2,3-dihydrobenzo[b]furan-5-yl carboxylic acid

A solution of 5-bromo-7-tert-butyl-3,3-dimethyl-2,3-dihydrobenzo[b]furan (12.4 g, 44.0 mmol) in freshly distilled THF (44 mL) is cooled to −78° C. under Ar, and a solution of n-butyl lithium (2.5M in hexane; 15.0 mL, 37.5 mmol) is added dropwise via syringe. A slight exotherm is apparent, and a milky suspension results. The suspension is allowed to warm to −20° C., and then is cooled to −50° C. To the resulting suspension is added a large excess of freshly pulverized solid CO₂. The resulting mixture is allowed to warm to 0° C. After 1 h, the mixture is partitioned between 0.1N NaOH (40 mL) and hexane (3×30 mL). The hexane layer is dried (MgSO₄), filtered and evaporated to yield 7-tert-butyl-3,3-dimethyl-2,3-dihydrobenzo[b]furan. The aqueous layer is acidified to pH 2 with 1N HCl, and is extracted with Et₂O (3×20 mL). The Et₂O layers are combined, dried (MgSO₄), filtered and evaporated to provide the desired carboxylic acid.

7-tert-butyl-3,3-dimethyl-2,3-dihydrobenzo[b]furan-5-yl carboxylic acid chloride To an ice-cold solution of 7-tert-butyl-3,3-dimethyl-2,3-dihydrobenzo[b]furan-5-yl carboxylic acid (3.99 g, 15.9 mmol) in THF (66 mL) and DMF (0.13 mL) is added dropwise oxalyl chloride (2.1 mL). After gas evolution ceases, the reaction is allowed to warm to 24° C. and stir for 2 h. The volatiles are evaporated to yield the chloride as a low melting solid.

N-propyl (7-tert-butyl-3,3-dimethyl-2,3-dihydrobenzo[b]furan-5-yl)-carboxamide

To a solution of (7-tert-butyl-3,3-dimethyl-2,3-dihydrobenzo[b]furan-5-yl) carboxylic acid chloride (450 mg, 1.69 mmol) in CH₂Cl₂ (10 mL) is added in a single portion n-propylamine (2 mL). After the exothermic reaction subsides, the mixture is evaporated and suspended in 1N HCl (10 mL). The insoluble material is filtered and crystallized from isopropanol/H₂O, to yield N-propyl (7-tert-butyl-3,3-dimethyl-2,3-dihydrobenzo[b]furan-5-yl)carboxamide as white needles.

Example 2

Synthesis of N-propyl (7-tert-butyl-3,3-dimethyl-2, 3-dihydrobenzo[b]furan-5-yl)thioamide

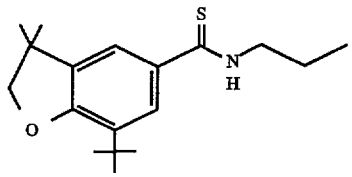

A mixture of N-propyl (7-tert-butyl-3,3-dimethyl-2,3-dihydrobenzo[b]furan-5-yl)carboxamide (188 mg, 0.65 mmol) and Lawesson's reagent (141 mg, 0.35 mmol) in dry toluene (7 mL) is refluxed in an argon atmosphere for 4.5 h. After removing toluene, the resulting solid is purified by flash chromatography (25% EtOAc/hexanes) to give N-propyl (7-tert-butyl-3,3-dimethyl-2,3-dihydrobenzo[b]furan-5-yl)thioamide as yellowish crystals.

Example 3

Synthesis of N-(7-tert-butyl-3,3-dimethyl-2,3-dihydrobenzo[b]furan-5-yl)-propanamide

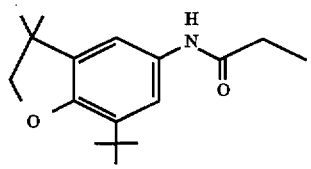

7-tert-butyl-3,3-dimethyl-5-nitro-2,3-dihydrobenzo [b]furan

A solution of 7-tert-butyl-3,3-dimethyl-2,3-dihydrobenzo [b]furan (10.0 g, 49.0 mmol) in glacial acetic acid 80 mL) is treated with 70% nitric acid (4.0 mL, 63.7 mmol) dropwise, and allowed to stir at 24° C. for 4 h. TLC (hexane) is used to monitor reaction progress. The reaction mixture is partitioned between Et₂O (100 mL) and H₂O (100 mL). The Et₂O layer is washed with H₂O (50 mL) and saturated Na₂CO₃ (50 mL), dried (MgSO₄), filtered and evaporated to a red solid (9.12 g). Crystallization from hexane provides 7-tert-butyl-3,3-dimethyl-5-nitro-2,3-dihydrobenzo[b]furan as an orange solid.

5-amino-7-tert-butyl-3,3-dimethyl-2,3-dihydrobenzo [b]furan

A mixture of 7-tert-butyl-3,3-dimethyl-5-nitro-2,3-dihydrobenzo[b]furan (2.2 g, 8.8 mmol) and 10% Pd on charcoal (220 mg) in EtOH (60 mL) is hydrogenated at 24° C. and 40 psi of H₂ for 3 h. The reaction is monitored by TLC (EtOAC:hexane, 1:19). The reaction mixture is vented to N₂, filtered through Celite, and evaporated to yield 5-amino-7-tert-butyl-3,3-dimethyl-2,3-dihydrobenzo[b] furan as a purple solid.

N-(7-tert-butyl-3,3-dimethyl-2,3-dihydrobenzo[b] furan-5-yl)propanamide

To a solution of 5-amino-7-tert-butyl-3,3-dimethyl-2,3-dihydrobenzo[b]furan (400 mg, 1.84 mmol) and dimethylaminopyridine (61 mg, 0.50 mmol) in CH₂Cl₂ (5 mL) is added at 24° C. propionyl chloride (160 μL, 1.84 mmol) in a single portion. The reaction is stirred for 1 h, and monitored by TLC (hexane:EtOAc, 9:1). The mixture is diluted with Et₂O (5 mL), and a fine precipitate is filtered off. The filtrate is evaporated to an orange solid which is purified by preparative TLC (hexane:EtOAc, 9:1) to yield N-(7-tert-butyl-3,3-dimethyl-2,3-dihydrobenzo[b]-furan-5-yl) propanamide as a white solid.

Example 4

Synthesis of N-(7-tert-butyl-3,3-dimethyl-2,3-dihydrobenzo[b]furan-5-yl)-acetamide

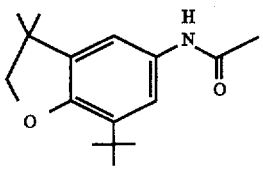

To a solution of 5-amino-7-tert-butyl-3,3-dimethyl-2,3-dihydrobenzo[b]-furan (400 mg, 1.84 mmol) and dimethylaminopyridine (247 mg, 2.024 mmol) in CH₂Cl₂ (20 mL) is added at 24° C. acetyl chloride (130 μL, 1.84 mmol) in a single portion. The reaction is stirred for 1 h, and monitored by TLC (hexane:EtOAc, 9:1). The mixture is diluted with Et₂O (5 mL), and a fine precipitate is filtered off. The filtrate is evaporated to an orange solid which is purified by preparative TLC (hexane:EtOAc, 9:1) to yield N-(7-tert-butyl-3,3-dimethyl-2,3-dihydrobenzo[b]furan-5-yl) acetamide as a white solid.

Compositions

Compositions of the subject invention comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

Compositions of the subject invention preferably comprise from about 0.1% to about 99.9% by weight of a compound, more preferably from about 20% to about 80%, and most preferably from about 40% to about 70%.

In addition to the compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tweens®; wetting agents such as sodium lauryl sulfate; coloring agents; flavoring agents, excipients; tableting agents; stabilizers; antioxidants; preservatives; pyrogen-free water; isotonic saline; and phosphate buffer solutions.

The choice of a pharmaceutically-acceptable carrier to be used in conjunction with a subject compound is basically determined by the way the compound is to be administered.

If the subject compound is to be injected, it is preferably injected non-intravenously; the preferred pharmaceutically-acceptable carrier is sterile, physiological saline, with blood compatible suspending agent, the pH of which has been adjusted to about 7.4. Such injectable compositions preferably comprise from about 1% to about 50% of the subject compound, more preferably from about 5% to about 25%, also preferably from about 10 mg to about 600 mg of the subject compound per dose.

Suitable pharmaceutically-acceptable carriers for topical application include those suited for use in lotions, creams, gels and the like. Topical compositions preferably contain from about 1% to about 50% of an emollient, more preferably from about 5% to about 25% of an emollient. Such topical compositions preferably comprise from about 0.1% to about 50%, of the subject compound, more preferably from about 0.5% to about 10%, also preferably from about 5 mg to about 3500 mg per dose.

The preferred mode of administering the subject compound is perorally. The preferred unit dosage form is therefore tablets, capsules and the like, comprising a safe and effective amount of the compound, which is preferably from about 5 mg to about 3500 mg, more preferably from about 10 mg to about 1000 mg, and most preferably from about 25 mg to about 600 mg. The pharmaceutically-acceptable carriers suitable for the preparation of unit dosage forms for oral administration are well-known in the art. Their selection will depend on secondary considerations like taste, cost, and shelf stability, which are not critical for the purposes of the subject invention, and can be made without difficulty by a person skilled in the art.

Many of the subject compounds are hydrophobic. If it is desired to provide an aqueous-based composition or a composition soluble in or miscible with aqueous media, a solubilizing agent may be included in the composition. Non-limiting examples of such solubilizing agents include polyethylene glycol, propylene glycol, ethanol, and polyoxyethylene (35) castor oil.

Particularly preferred oral composition carriers suitable for compositions of the subject invention are disclosed in U.S. Pat. No. 5,189,066 of Kelm & Bruns, issued Feb. 23, 1993, entitled "Pharmaceutical Compositions of Tebufelone", and U.S. Pat. No. 5,281,420 of Kelm & Dobrozsi, issued Jan. 25, 1994, entitled "Solid Dispersion Compositions of Tebufelone", hereby incorporated herein by reference.

Methods

Another aspect of the subject invention is methods for treating or preventing diseases characterized by inflammation by administering a safe and effective amount of a subject compound to a human or lower animal in need of such treatment. The term "diseases characterized by inflammation", as used herein, means conditions which are known to involve inflammation, and may include conditions such as arthritis (e.g., rheumatoid arthritis, osteoarthritis, psoriatic arthritis, juvenile arthritis, Reiter's syndrome, infectious arthritis, and ankylosing spondylitis, systemic lupus, erythematosus and gout), as well as the presence of inflammation whether or not it is associated with an identifiable disease. Diseases characterized by inflammation further may include inflammation in the oral cavity (e.g., inflammation associated with gingivitis or periodontal disease); inflammation in the gastrointestinal tract, (e.g., inflammation associated with ulcers and irritable bowel disease); inflammation associated with dermatological diseases (e.g., psoriasis, acne, and other skin inflammation); inflammation associated with the respiratory tract (e.g., asthma, bronchitis, and allergies); and inflammation in the central nervous system (e.g., Alzheimer's disease).

Another aspect of the subject invention is methods for treating or preventing pain by administering a safe and effective amount of a subject compound to a human or lower animal in need of such treatment. Pain which can be treated or prevented by administering the subject compounds may include peripheral pain, menstrual pain, dental pain, and lower back pain.

Another aspect of the subject invention is methods for preventing oxidative damage at inflammatory sites by administering a safe and effective amount of a subject compound to a human or lower animal in need of such treatment. While not limited to a particular mechanism, it is believed that the subject compounds inhibit leukotriene synthesis, thereby decreasing neutrophil accumulation at an inflammatory site.

Another aspect of the subject invention is methods for treating or preventing gastric or duodenal ulcers or erosions by administering a safe and effective amount of a subject compound to a human or lower animal in need of such treatment. In particular, such ulcers or erosions caused by ethanol or non-steroidal antiinflammatory drugs (NSAIDs) can be treated and/or prevented by administration of preferred subject compounds.

Appropriate tests for determining the gastrointestinal safety or gastroprotective or gastric healing properties of the subject compounds are known.

Methods for determining acute gastrointestinal safety are disclosed and/or referred to in the following references: Unangst, P. C., G. P. Shrum, D. T. Connor, R. D. Dyer, and D. J. Schrier, "Novel 1,2,4-Oxadiazoles and 1,2,4-Thiadiazoles as Dual 5-Lipoxygenase and Cyclooxygenase Inhibitors", *J. Med. Chem.*, Vol. 35 (1992), pp. 3691–3698; and Segawa, Y, O. Ohya, T. Abe, T. Omata, et al., "Anti-inflammatory, Analgesic, and Antipyretic Effects and Gastrointestinal Toxicity of the New Anti-inflammatory Drug N-{3-[3-(piperidinylmethyl)phenoxy] propyl}-carbamoylmethylthio]ethyl 1-(p-chlorobenzoyl) 5-Methoxy-2methyl-3-indolylacetate", *Arzneim.-Forsch./Drug Res.*, Vol. 42 (1992), pp. 954–992. In the methods disclosed therein, stomachs of the animals are typically examined two hours after dosing a compound. Methods for determining subchronic gastrointestinal safety are disclosed and/or referred to in the following references: Melarange, R., C. Gentry, et al., "Anti-inflammatory and Gastrointestinal Effects of Nabumetone or Its Active Metabolite, 6-Methoxy-2-naphthylacetic Acid (6MNA)", *Dig. Dis. Sci.*, Vol. 37 (1992), pp. 1847–1852; and Wong, S., S. J. Lee, et al., "Antiarthritic Profile of BF-389—A Novel Anti-inflammatory Agent With Low Ulcerogenic Liability", *Agents Actions*, Vol. 37 (1992), pp. 90–91.

Methods for determining acute gastroprotection are disclosed and/or referred to in the following reference: Playford, R. J., D. A. Versey, S. Haldane, M. R. Alison, and J. Calan, "Dose-dependent Effects of Fentanyl on Indometharin-induced Gastric Damage", *Digestion*, Vol. 49 (1991), pp. 198–203. In the method disclosed therein, female Lewis rats (130–175 g) are dosed perorally with the subject compound (40 mg/kg b.i.d.) or vehicle at 2 hours and immediately before administration of a gastric damaging dose of indomethacin. The rats are sacrificed 4 hours later by $CO_2$ asphyxiation. Gastric corpus damage (millimeters of hemorrhagic lesions) is measured by digitized imaging.

The preferred mode of administration of the subject compounds is peroral, but other known methods of administration are contemplated as well, e.g., dermatomucosally (for example, dermally, rectally and the like), and parenterally (for example, by subcutaneous injection, intramuscular injection, intraarticular injection, intravenous injection and the like). Ocular administration and inhalation are also included. Thus specific modes of administration include, without limitation, peroral, transdermal, mucosal, sublingual, intranasal, intramuscular, intravenous, intraperitoneal, subcutaneous, and topical administration.

Preferred doses of the subject compounds range from about 0.2 mg/kg to about 70 mg/kg, more preferably from about 0.5 mg/kg to about 12 mg/kg. Preferred injectable doses comprise from about 0.1 mg/kg to about 10 mg/kg of the subject compound. Preferred topical doses comprise from about 1 mg/cm$^2$ to about 200 mg/cm$^2$ of the subject compound applied to the skin surface. Preferred peroral doses comprise from about 0.5 mg/kg to about 50 mg/kg, more preferably from about 1 mg/kg to about 20 mg/kg, more preferably still from about 2 mg/kg to about 10 mg/kg, of the subject compound. Such doses are preferably administered from about once to about six times daily, more preferably from about twice to about four times daily. Such daily doses are preferably administered for at least one week, also preferably for at least two weeks, also preferably at least one month, also preferably for at least 2 months, also preferably for at least 6 months, 1 year, 2 years, or more.

COMPOSITIONS AND METHOD EXAMPLES

The following non-limiting examples illustrate the subject invention.

Example A

Pharmaceutical compositions in the form of tablets are prepared by conventional methods, such as mixing and direct compaction, formulated as follows:

| Ingredient | Quantity (mg per tablet) |
|---|---|
| Compound 11 | 200 |
| Microcrystalline Cellulose | 100 |
| Sodium Starch Glycollate | 30 |
| Magnesium Stearate | 3 |

When administered orally two times daily, the above composition significantly reduces the inflammation in a patient suffering from rheumatoid arthritis. A significant benefit is also achieved by twice daily administration of this composition to a patient suffering from osteoarthritis.

Example B

A pharmaceutical composition in capsule form is prepared by conventional methods, formulated as follows:

| Ingredient | Quantity (mg per capsule) |
| --- | --- |
| Compound 3 | 200 |
| Lactose | To fill to volume of capsule |

The above capsule administered orally once a day substantially reduces the symptomology of a patient afflicted with rheumatoid arthritis or osteoarthritis.

Example C

A pharmaceutical composition in liquid form is prepared by conventional methods, formulated as follows:

| Ingredient | Quantity |
| --- | --- |
| Compound 18 | 200 mg. |
| EtOH | 4 ml |
| Methyl cellulose | 0.4 mg |
| Distilled water | 76 ml |
| Tween 80 | 1.6 ml |

50 ml of the above composition administered perorally once a day substantially reduces the symptoms of a patient afflicted with rheumatoid arthritis or osteoarthritis.

Example D

A pharmaceutical composition in liquid form is prepared by conventional methods, formulated as follows:

| Ingredient | Quantity |
| --- | --- |
| Microcrystalline (micronoized) Compound 2 | 200 mg |
| Avicel (microcrystalline cellulose) | 50 mg |
| Tween 80 | 1.6 ml |
| Methyl cellulose | 0.4 mg |
| Deionized water | 80 ml |

100 ml of the above composition administered perorally twice a day substantially reduces the symptoms of a patient afflicted with rheumatoid arthritis or osteoarthritis.

Example E

An oral solid pharmaceutical composition is prepared by conventional methods, formulated as follows:

| Ingredient | Quantity (% by weight) |
| --- | --- |
| Compound 16 | 20 |
| Pluronic F108 | 40 |
| Tween 80 | 40 |

Example F

An oral solid pharmaceutical composition is prepared by conventional methods, formulated as follows:

| Ingredient | Quantity (% by weight) |
| --- | --- |
| Compound 3 | 50 |
| Triglycerides and derivatives | 45 |
| Cremaphor EL | 5 |

While particular embodiments of the subject invention have been described, it would be obvious to those skilled in the art that various changes and modifications to the compositions disclosed herein can be made without departing from the spirit and scope of the invention. It is intended to cover, in the appended claims, all such modifications that are within the scope of this invention.

We claim:

1. A compound having the structure:

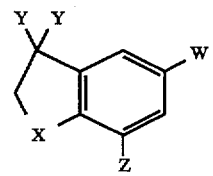

wherein (a) W is C(X')NRR' or NRC(X')R';

(b) X and X' are each independently O or S;

(c) each Y is independently hydrogen or unsubstituted straight, branched or cyclic alkanyl having from 1 to about 3 carbon atoms, or the two Y's are bonded to form an alkanyl ring having from 3 to about 7 carbon atoms;

(d) Z is unsubstituted branched or cyclic alkyl, or unsubstituted or alkanyl-substituted phenyl or benzyl, Z having from 3 to about 10 atoms other than hydrogen;

(e) R and R' are each selected from hydrogen, hydroxy, straight, branched or substituted or unsubstituted alkyl having from 1 to about 6 carbon atoms, and cyclic alkyl having from 3 to about 7 carbon atoms; unsubstituted or substituted aryl, heteroaryl or heterocyclic groups; or R and R' are bonded together to form a ring having from about 3 to about 8 atoms wherein from about 1 one to about 4 atoms may be heteroatoms.

2. The compound of claim 1 wherein X is oxygen and R is hydrogen or methyl.

3. The compound of claim 1 wherein each Y is independently selected from the group consisting of hydrogen, methyl and ethyl; and Z is selected from the group consisting of unsubstituted $C_4$–$C_6$ branched alkanyl having 2 branches, unsubstituted $C_3$–$C_6$ cycloalkanyl, and unsubstituted phenyl.

4. The compound of claim 3 wherein R is hydrogen, both Y are methyl, and Z is t-butyl.

5. The compound of claim 3 wherein R is hydrogen or methyl, and R' is $C_1$–$C_6$ straight or single-branched alkyl or straight alkyl with a terminal cyclic alkyl, saturated or unsaturated with one double bond between non-terminal carbon atoms, or $C_3$–$C_6$ cycloalkanyl.

6. The compound of claim 5 wherein X is oxygen, and R' is unsubstituted.

7. The compound of claim 6 wherein both Y are methyl, and Z is t-butyl.

8. The compound of claim 3 wherein R is hydrogen or methyl, and R' is selected from the group consisting of methyl, ethyl, n-propyl, i-propyl, n-butyl, I-methylbutyl, ethoxy, benzyl, phenethyl, 2-methoxyethyl, 2-thiazolyl, 2-thiazolinyl, and 3-pyridyl.

9. The compound of claim 8 wherein both Y are methyl, and Z is t-butyl.

10. The compound of claim 9 wherein X is oxygen, and R is hydrogen.

11. The compound of claim 8 wherein R' is selected from the group consisting of methyl, ethyl, n-propyl, n-butyl and ethoxy.

12. The compound of claim 11 wherein R is hydrogen, both Y are methyl, Z is t-butyl, and both X and X' are oxygen.

13. The compound of claim 3 wherein R and R' are bonded to together to form a ring having from about 3 to about 7 atoms, wherein from about 1 to about 3 atoms are heteroatoms.

14. The compound of claim 13 wherein the ring formed by R and R' is selected from the group consisting of pyrrolidinyl, piperidinyl, thiomorpholinyl, piperazinyl and morpholinyl.

15. A composition comprising a compound of any of claims 1, 4, 10 and 13 and a pharmaceutically-acceptable carrier.

16. A method of treating inflammation or pain comprising administation, to a human or lower animal in need of such treatment, of a safe and effective amount of a compound of any of claims 1, 4, 10 and 13.

17. A method of treating arthritis comprising daily peroral administration, to a human in need of such treatment, of from about 1 mg/kg to about 20 mg/kg of a compound of any of claims 1, 4, 10 and 13.

* * * * *